(12) United States Patent
Gourlay et al.

(10) Patent No.: US 9,132,225 B2
(45) Date of Patent: Sep. 15, 2015

(54) CARDIOPULMONARY BYPASS CIRCUIT INCLUDING A FILTRATION DEVICE

(75) Inventors: Terence Gourlay, Erskine (GB); Stephen Cotton, Nottingham (GB)

(73) Assignee: Brightwake Limited, Nottingham, Nottinghamshire (GB)

( * ) Notice: Subject to any disclaimer, the term of this patent is extended or adjusted under 35 U.S.C. 154(b) by 0 days.

(21) Appl. No.: 13/144,651

(22) PCT Filed: Jan. 15, 2010

(86) PCT No.: PCT/GB2010/050061
§ 371 (c)(1),
(2), (4) Date: Jul. 14, 2011

(87) PCT Pub. No.: WO2010/082064
PCT Pub. Date: Jul. 22, 2010

(65) Prior Publication Data
US 2011/0272343 A1 Nov. 10, 2011

(30) Foreign Application Priority Data

Jan. 15, 2009 (GB) .................................. 0900558.8
Jun. 12, 2009 (GB) .................................. 0910104.9
Dec. 4, 2009 (GB) .................................. 0921265.5

(51) Int. Cl.
*A61M 1/36* (2006.01)
*B01D 29/07* (2006.01)
(Continued)

(52) U.S. Cl.
CPC ........... *A61M 1/3679* (2013.01); *B01D 39/083* (2013.01); *B01D 39/1623* (2013.01);
(Continued)

(58) Field of Classification Search
CPC .. B29C 65/00; B29C 65/02; B29C 66/81433; B29C 65/086; B29C 66/21; B29C 66/45; B29C 66/83411; B29C 66/7294; B29C 66/729; B29C 66/9516; A61M 1/3679; B01D 2239/0407; B01D 2239/0677; B01D 2239/0681; B01D 2239/069; B01D 2239/086; B01D 2239/1216; B01D 2239/1241; B01D 39/1623; B01D 39/2055; B01D 39/083; B29K 2067/00; B29K 2105/048; B29K 2105/0854; B29K 2105/16; B29L 2009/00; B29L 2031/14

See application file for complete search history.

(56) References Cited

U.S. PATENT DOCUMENTS 3,765,536 A * 10/1973 Rosenberg .................... 210/446
3,971,373 A * 7/1976 Braun ...................... 128/206.19
(Continued)

FOREIGN PATENT DOCUMENTS

DE 19512005 A1 8/1995
DE 10058512 A1 6/2002
(Continued)

OTHER PUBLICATIONS

D.J. Malik et al, Preparation of novel mesoporous carbons for the adsorption of an inflammatory cytokine (IL-1beta), 2004, Biomaterials, 25, 2933-2940.*
(Continued)

*Primary Examiner* — John Kim
(74) *Attorney, Agent, or Firm* — LeClairRyan, a Professional Corporation

(57) ABSTRACT

Apparatus and methods for extracorporeal blood filtration involving the connection of a patient's cardiovascular circulation to an extracorporeal circulatory circuit, and filtration devices suitable for use in such apparatus and methods are disclosed. Such filtration devices include a filter medium comprising a layer of non-woven fabric (21) impregnated with porous beads (22) and carrying a porous screen (23) on at least one side. This invention enables the removal or particular molecular species such as pro-inflammatory cytokines from a patient's circulation, and is of particular utility in cardiopulmonary bypass and haemodialysis-like procedures.

18 Claims, 7 Drawing Sheets

(51) Int. Cl.
    *B01D 39/08*       (2006.01)
    *B01D 39/16*       (2006.01)
    *B01D 39/20*       (2006.01)
    *B29C 65/00*       (2006.01)
    *B29C 65/08*       (2006.01)
    *B29C 65/02*       (2006.01)
    *B29K 67/00*       (2006.01)
    *B29K 105/04*     (2006.01)
    *B29K 105/08*     (2006.01)
    *B29K 105/16*     (2006.01)
    *B29L 9/00*        (2006.01)
    *B29L 31/14*      (2006.01)

(52) U.S. Cl.
    CPC ............ *B01D39/2055* (2013.01); *B29C 65/02* (2013.01); *B29C 65/086* (2013.01); *B29C 66/21* (2013.01); *B29C 66/45* (2013.01); *B29C 66/729* (2013.01); *B29C 66/7294* (2013.01); *B29C 66/83411* (2013.01); *B01D 2239/0407* (2013.01); *B01D 2239/069* (2013.01); *B01D 2239/0677* (2013.01); *B01D 2239/0681* (2013.01); *B01D 2239/086* (2013.01); *B01D 2239/1216* (2013.01); *B01D 2239/1241* (2013.01); *B29C 66/81433* (2013.01); *B29C 66/9516* (2013.01); *B29K 2067/00* (2013.01); *B29K 2105/048* (2013.01); *B29K 2105/0854* (2013.01); *B29K 2105/16* (2013.01); *B29L 2009/00* (2013.01); *B29L 2031/14* (2013.01)

(56) References Cited

U.S. PATENT DOCUMENTS

| | | | |
|---|---|---|---|
| 4,414,970 A | | 11/1983 | Berry |
| 4,728,432 A | | 3/1988 | Sugiyama et al. |
| 4,784,892 A | | 11/1988 | Storey et al. |
| 5,409,761 A | | 4/1995 | Langley |
| 5,540,841 A | * | 7/1996 | Gsell et al. ................... 210/645 |
| 5,540,976 A | | 7/1996 | Shawver et al. |
| 5,830,311 A | | 11/1998 | Braun et al. |
| 5,865,919 A | | 2/1999 | Megchelsen et al. |
| 5,879,494 A | | 3/1999 | Hoff et al. |
| 5,911,883 A | | 6/1999 | Anderson |
| 6,074,966 A | | 6/2000 | Zlatkus |
| 2003/0121588 A1 | | 7/2003 | Pargass et al. |
| 2005/0045566 A1 | | 3/2005 | Larkin et al. |
| 2005/0136224 A1 | | 6/2005 | Nickel et al. |
| 2005/0276956 A1 | | 12/2005 | Zink, II et al. |
| 2008/0223776 A1 | * | 9/2008 | Sumian et al. ............. 210/257.1 |

FOREIGN PATENT DOCUMENTS

| | | | |
|---|---|---|---|
| EP | 0425270 | A2 | 5/1991 |
| EP | 1112823 | A2 | 7/2001 |
| EP | 1430911 | A2 | 6/2004 |
| EP | 1634698 | A2 | 3/2006 |
| EP | 1790467 | A1 | 5/2007 |
| EP | 1880840 | A1 | 1/2008 |
| GB | 1440027 | A | 6/1976 |
| GB | 2290747 | A | 1/1996 |
| WO | 9402090 | A1 | 2/1994 |
| WO | 9841095 | A2 | 9/1998 |
| WO | 0046021 | A1 | 8/2000 |
| WO | 0187592 | A1 | 11/2001 |
| WO | WO 2005123952 A2 * | | 12/2005 |
| WO | 2007046806 | A1 | 4/2007 |
| WO | 2007091931 | A1 | 8/2007 |
| WO | 2007113597 | A2 | 10/2007 |
| WO | 2008088281 | A1 | 7/2008 |
| WO | 2009128757 | A1 | 10/2009 |
| WO | 2010052485 | A1 | 5/2010 |
| WO | 2010061228 | A1 | 6/2010 |

OTHER PUBLICATIONS

Malik, D. J., et al. "Preparation of novel mesoporous carbons for the adsorption of an inflammatory cytokine (IL-1 *β*)." Biomaterials 25.15 (2004): 2933-2940.*

International Search Report for corresponding application PCT/GB2010/050061, dated Aug. 19, 2010.

Great Britain Search Report for corresponding application GB0900558.8, dated Nov. 16, 2009.

* cited by examiner

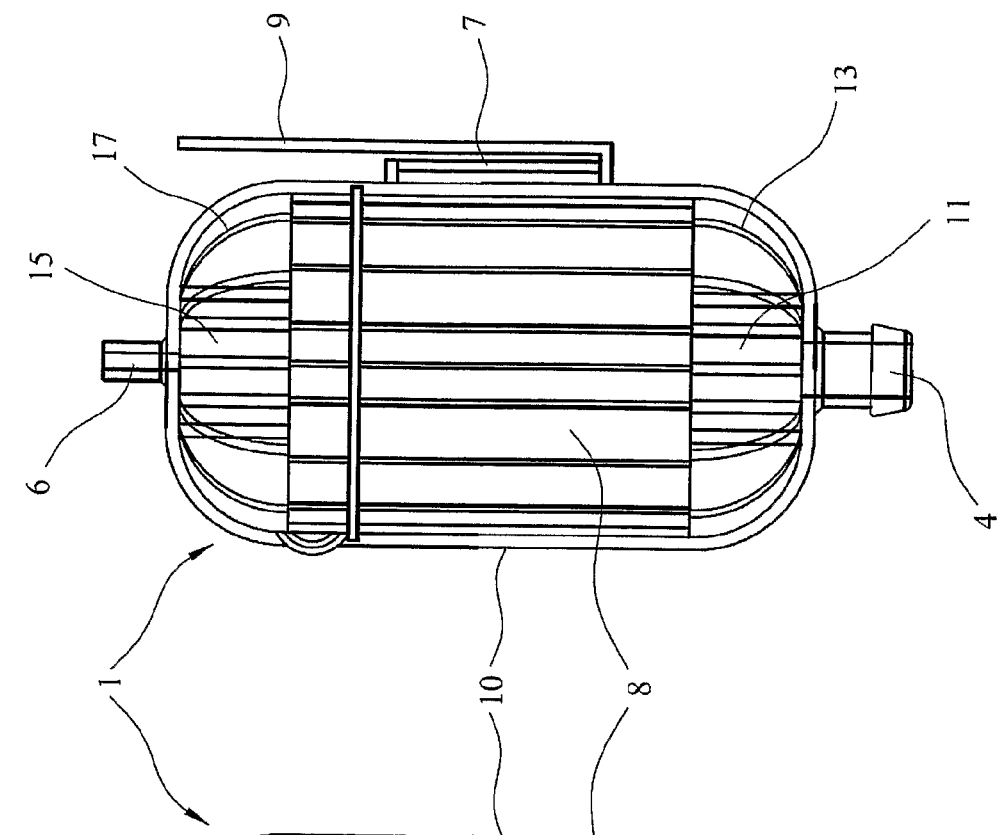

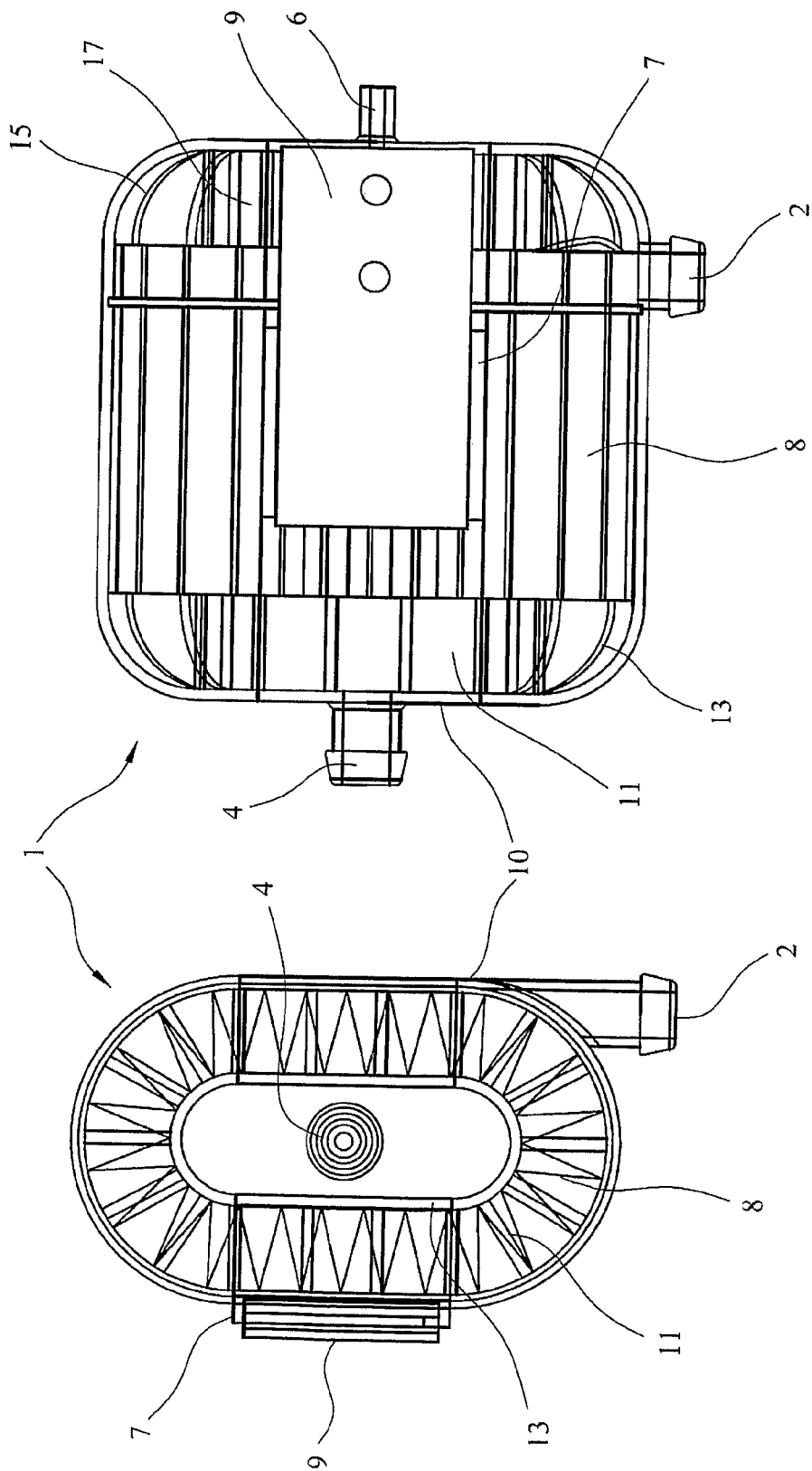

CARDIOPULMONARY BYPASS CIRCUIT INCLUDING A FILTRATION DEVICE

This application is a national stage application under 35 U.S.C. §371 of PCT Application No. PCT/GB2010/050061, filed Jan. 15, 2010, which claims the priority benefit of Great Britain Application Nos. GB0900558.8, filed Jan. 15, 2009, GB0910104.9, filed Jun. 12, 2009, and GB0921265.5, filed Dec. 4, 2009.

The present invention relates to apparatus and methods for extracorporeal blood filtration, and to filtration devices suitable for use in such apparatus and methods.

Major surgical procedures such as cardiac, vascular and trauma surgery, generally cause significant tissue trauma, which often leads to an excessive cytokine-mediated inflammatory reaction. This inflammation may cause significant post-operative complications such as tissue necrosis, nerve damage, delayed wound healing and pain or discomfort for the patient. It is therefore desirable to reduce the effects of pro-inflammatory cytokines and other molecular species that are responsible for this excessive inflammatory reaction. During such major surgical procedures, a cardiopulmonary bypass (CPB) is often performed, in which the circulation and oxygenation of the blood is temporarily taken over by an artificial heart-lung machine. During CPB, the blood is often filtered before being re-introduced into the body. There is a need for blood filters used in CPB to remove undesirable materials from the blood effectively, whilst at the same time maintaining a satisfactory rate of blood flow through the filter. Moreover, conventional filters are only intended to remove air and debris such as cellular aggregates and clots. It would therefore be beneficial to provide a filter that is capable of removing the pro-inflammatory cytokines and other molecular species responsible for excessive post-operative inflammation, along with the air and debris.

In addition to this, pro-inflammatory cytokines are implicated in a range of widespread chronic inflammatory diseases such as rheumatoid arthritis, Crohn's disease and inflammatory bowel disease. The treatment of these diseases often involves attenuation of the function of these pro-inflammatory cytokines and is generally achieved with the use of a range of small molecule drugs and monoclonal antibodies. These have a number of disadvantages including short half-life and toxicity, as well as the enormous expense of their development and, in the case of monoclonal antibodies, their manufacture. Alternative methods for the treatment of such cytokine-mediated chronic inflammatory diseases are therefore potentially very beneficial.

There has now been devised apparatus for extracorporeal blood filtration that overcomes or substantially mitigates problems associated with the prior art and/or addresses the needs described above.

According to a first aspect of the invention, there is provided apparatus for extracorporeal blood filtration, said apparatus including a filtration device comprising a housing having inlet and outlet ports and a filter medium disposed in a blood flow path between said inlet and outlet ports, wherein the filter medium comprises a non-woven fabric having porous beads dispersed therein and carrying a porous screen on at least one side thereof.

The apparatus according to the invention is advantageous in that it effectively filters the blood passing through it, removing from the blood emboli such as gas bubbles, cellular aggregates, tissue fragments, and the like. The filter medium may also be effective in removing from the blood pro-inflammatory cytokines and other pro-inflammatory molecules that are activated or generated during the surgical procedure, or that are over-produced by the body in immune system related disorders.

The filtration device contains a filter medium that is in intimate contact with the blood passing through the filtration device. The filter medium is formed from a sheet of material comprising a non-woven fabric with a porous screen on at least one side thereof.

Suitable non-woven fabrics have a permeable and open structure that facilitates the passage of blood without causing undue stress to blood cells. The porous open structure also provides a large surface area for the attachment of porous beads to enhance contact between the beads and the blood.

Suitable non-woven materials may be produced by various methods. However, preferred materials for use in the invention are produced by air-laying. Airlaid non-woven materials are therefore a preferred class of nonwoven materials for use in the invention.

Airlaid non-woven material is manufactured by dispersing fibres into a fast moving air stream and condensing them in progressive layers onto a screen using either pressure or a vacuum, to produce an airlaid web. These fibres are then bonded either by heat (thermal bonding), involving heating an airlaid web composed of synthetic fibres to the point where the fibres fuse together, or using a synthetic binding substance (latex bonding). A combination of these methods may also be used (multi-bonding), where an airlaid material is produced by thermal bonding, followed by spraying with a synthetic binder to reduce lint release. The process of producing airlaid nonwoven material is highly controllable and it is possible to incorporate a range of different fibres, or fibre densities, into a single layer of material. Consequently, the manufacturing process can be tailored to provide wound packing materials with a variety of properties, so the porosity and firmness may be varied depending on the particular application.

For use in the present invention, it is most desirable to use thermally bonded airlaid non-woven material because the process is cleaner than the alternatives that involve the introduction of a binding agent into the material.

The non-woven material used in the invention may be manufactured from fibres of a wide range of materials. Most preferably, the material is a synthetic polymeric material. A wide range of synthetic polymeric materials may be employed, including polyesters, polyacrylics, polyamides, polyolefins and polylactides, amongst many others.

A particularly preferred material for use in the invention is polyester.

One particularly suitable non-woven fabric for use in the invention is air-laid, thermally bonded non-woven fabric sold under the trade name AEROFILL by Libeltex BVBA (Marialoop Steenweg 51, BE-8760 Meulebeke, Belgium). Such materials are available in a range of grades, and a wide range of such grades may be suitable for use in the invention. For instance, the non-woven fabric may have a weight of up to 500 g/m² or more. More commonly, however, the weight of the non-woven fabric may be up to 200 g/m² or up to 100 g/m², typically between 20 g/m² and 200 g/m², or between 20 g/m² and 100 g/m², eg about 50 g/m².

The non-woven fabric acts as a support medium for the porous beads that are dispersed in it. The beads may simply be captivated within the fibres of the non-woven fabric, but are preferably attached to the fibres of the fabric by suitable means, such as by an adhesive. Suitable adhesives are preferably hypoallergenic to reduce the risk of provoking an adverse reaction when the blood is re-introduced into the patient. Suitable adhesives include cyanoacrylates and epoxy adhesives, but a particularly preferred adhesive is acrylic adhesive. The use of adhesive to secure the beads to the non-woven fabric is particularly beneficial, as it is relatively easy to perform and is easy to control. Individual beads can be anchored to a plurality of fibres within the fabric, typically by pedicles of adhesive that extend between the bead and surrounding fibres. Such an approach is much easier and reliable than, for instance, immobilisation of the beads by chemical bonds, which typically requires functionalisation of the beads and/or the fibres of the non-woven material, and may be possible only for beads of certain materials.

Attachment of the beads to the fibres of the non-woven fabric is particularly desirable as it prevents the beads being dislodged from the fabric as blood is passed through the filtration device at the relatively high flow rates that are conventionally employed in extracorporeal blood filtration applications. Apart from reducing the efficacy of the filtration device, migration of the beads from the fabric could lead to accumulation of beads on the porous screen downstream of the non-woven fabric, potentially blocking the pores in that screen and leading to a reduction in flow rate and/or an increase in pressure drop across the filter medium.

Thus, according to another aspect of the invention, there is provided a filtration device for extracorporeal blood filtration, the device comprising a housing having inlet and outlet ports and a filter medium disposed in a blood flow path between said inlet and outlet ports, wherein the filter medium comprises a non-woven fabric having porous beads dispersed therein and carrying a porous screen on at least one side thereof, wherein the porous beads are anchored to the non-woven fabric by means of adhesive.

The porous screen or screens are sheets of material having pores of a regular diameter, for the removal of debris from the fluid stream. The porous screen is most preferably a synthetic plastics material, with pores of a suitable size to prevent the passage through the filter medium of emboli in the blood and to retain the porous beads within the filter medium. Typically, the screen is formed of polyester material, eg a woven polyester. Typically, the screen has pores that are between 20 µm and 100 µm in size. Porous screens that are particularly preferred are 40 µm filter screens commonly used for blood filtration. Suitable porous screens may be manufactured using a wide variety of materials. However, suitable materials are generally microporous films of synthetic plastics material, eg polyester.

Although a porous screen may be fitted on just one side of the non-woven fabric, porous screens are most preferably provided on both sides of the non-woven fabric.

The pores of the porous screens are preferably smaller in diameter that the porous beads in order to prevent any porous beads that become detached from the filter medium from entering the fluid stream. In this case, in embodiments of this invention where the filter medium comprises only one porous screen, that porous screen is preferably positioned on the downstream side of the filter medium, ie the side from which, in use, blood flows from the filter medium and is returned to the body. As noted above, however, porous screens are preferably provided on both sides of the non-woven fabric, in which case the filter medium comprises a central layer of non-woven fabric having porous beads dispersed therein and outer layers of porous screen material on each side of the central layer.

The porous beads may be formed out of any of a variety of materials, including porous carbon, pyrolysed polymer, zeolite, or any other porous nanostructure. Particularly preferred beads are mesoporous carbon beads formed of polymeric carbon. Beads of this type are able to absorb particular molecular species in a manner that is dependent on pore size. The size of the pores in the beads may vary widely depending on the target molecular species, but will generally be between 0.2 and 50 nm in diameter.

The porous beads are generally between 50 µm and 500 µm in diameter, more preferably between about 100 µm and 300 µm, eg about 200 µm in diameter. It has been found that smaller diameter beads are more effective at removing target molecular species. However, smaller beads are more difficult to produce and also require non-woven fabrics of less open structure for entrapment of the beads, resulting in a greater pressure drop across the filter medium, potentially leading to haemolysis and activation of white blood cells during use. The porous beads may generally not be smaller in diameter than the pores of any porous screen that is positioned on the downstream side of the filter medium, so that any beads that are displaced from the non-woven material are unable to pass through the porous screen.

Suitable mesoporous carbon beads for use in the invention are commercially available from numerous suppliers, including MAST Carbon International, Henley Park, Guildford, Surrey, GU3 2AF, United Kingdom.

The beads may be loaded into the non-woven fabric at a range of densities, eg between 0.2 and 10 g/m$^2$, or between 0.5 and 5 g/m$^2$, more typically from 0.5 to 4 g/m$^2$, eg about 2 g/m$^2$.

The filter medium preferably has a pleated configuration to increase the effective surface area of filter medium available for filtration. The overall surface area of filter medium will preferably be in excess of 0.01 m$^2$, eg about 0.1 m$^2$ or more. Most preferably, the filter medium is formed into an annular configuration with a central lumen, and is fixedly mounted within the housing such that blood is introduced, in use, into the space between the internal walls of the housing and the exterior of the filter medium, and flows through the filter medium to the central lumen, or vice versa. In such arrangements, the space exterior to the filter medium and the central lumen are in fluid communication with the inlet port and outlet port, or vice versa.

The filter medium is constructed by fastening a porous screen to at least one side of a bead-impregnated non-woven fabric. This is preferably carried out by ultrasonic welding.

Thus, according to another aspect of the invention, there is provided a method of producing a filter medium comprising a non-woven fabric having porous beads dispersed therein and carrying a porous screen on at least one side thereof, which method involves applying pressure and high-frequency vibrations to a multitude of points on the surface of a layered arrangement of bead-impregnated non-woven fabric and at least one porous screen, such that the layers of the layered arrangement are bonded together at those points.

The high frequency mechanical vibrations cause the generation of localised heat by friction, causing the layers of material to melt and weld together at these points. This process is particularly desirable because, unlike other fastening methods, it does not involve the introduction of any foreign elements such as adhesives or threads into the material. This is of particular relevance for materials for use in the medical industry, where contamination of the material could be a serious hazard.

Ultrasonic welding machines generally consist of three main components: a converter which uses disks of piezoelectric material to convert electrical energy into high frequency vibrations, an amplitude modifier (referred to as a booster) which increases the amplitude of the vibrations, and a sonotrode (referred to as a horn) which transmits the vibrations to the material. Welding is carried out by applying vibrations to material held under pressure between the sonotrode and a holding surface (referred to as an anvil).

In one particularly preferred method for production of the filter medium, a layered arrangement of bead-impregnated non-woven fabric and porous screen(s) is fed to a roller that has a multitude of regularly spaced flat-tipped pin-like projections on its surface. This so-called pin-roller and the sonotrode are configured so when the pin-roller is rotated, the tips of the pins pass close to the sonotrode surface. In operation, the layered arrangement is fed between the sonotrode and the pin-roller, and the tips of the pins act as points of increased pressure between the pin-roller and the sonotrode where welding can occur. In this way, the tips of the pins act as a multitude of individual holding surfaces or "anvils". The separate layers of material are welded together at the points where the tips of the pins squeeze the layers together ie weld-points. The use of the pin-roller allows ultrasonic welding to be carried out as a continuous process and, because only the regions of the material that contact the tips of the pins are welded, the properties of the remaining material are preserved.

The distribution and spacing of the weld-points correspond to the distribution and spacing of pin-like projections on the pin-roller. Weld-points are typically regularly arranged with a separation substantially greater than their diameter, although variation in the distribution of the weld-points is possible.

Thus, in a further aspect, the invention provides a filter medium comprising a non-woven fabric having porous beads dispersed therein and carrying a porous screen on at least one side thereof, wherein the non-woven fabric and porous screen(s) are bonded together at discrete weld points arranged at intervals across substantially the full extent of the filter medium.

The size of the weld-points also corresponds to the shape of the cross section of the pin-like projections on the pin-roller. Weld-points may vary considerably in size, but are typically between 0.5 mm and 2 mm in diameter, although smaller and larger weld-points may be possible.

The filter medium produced as described above is typically initially in the form of a long strip, which may be wound onto a roll for storage as an intermediate product prior to use in the manufacture of a finished product. The width of the strip generally does not exceed 200 mm, although the use of strips with greater widths is possible. For manufacture of the filtration device, the strip of filter medium is cut to size, and may be pleated and formed into an annular configuration, prior to insertion into the housing.

The filter medium is enclosed within a housing. The housing will preferably be formed of a durable and rigid material which is able to maintain the integrity of the filtration device. Typically, the housing comprises a plurality of housing components formed in plastics material, eg by injection moulding. Most commonly, the housing comprises two cooperating housing components.

The housing must have at least two ports, at least one for blood to enter the device and at least one for blood to exit the device, such that blood may pass through the filtration device continuously. The filter medium is preferably disposed within the housing so that the blood passes directly through the filter medium before it exits the filtration device via the exit port.

Entry of gas into vascular circulation is particularly undesirable as gas bubbles may become lodged within smaller blood vessels causing restriction of blood flow (air embolism). Larger volumes of gas may also become lodged in the heart, leading to circulatory arrest. In order to reduce the risk of this occurring, all gas should be flushed out of the filtration device before use. This will preferably be carried out by priming the filtration device with a priming fluid, such as sterile saline. The housing will therefore also be provided with a vent, to allow gas to escape from the housing as it is displaced by the priming fluid. The vent will preferably be located on the housing in such a way that all gas within the housing is expelled through the vent without the formation of air pockets.

The filtration device according to this invention may be included in an extracorporeal blood circulatory system, ranging from a small scale circuit similar to that used for kidney dialysis, to a higher throughput circuit such as that used during major surgery wherein the normal function of a patient's heart and lungs is taken over by an artificial heart-lung machine.

During a cardiopulmonary bypass procedure, the normal function of a patient's heart and lungs is taken over by a cardiopulmonary bypass circuit having an artificial heart-lung machine. Although high doses of anticoagulants are often used, blood clots and cellular aggregates, as well as gas bubbles, frequently form in the circuit and must be removed before the blood is returned to the patient. This is conventionally carried out with the use of a 40 µm filter. The filter device according to this invention will preferably be positioned in the cardiopulmonary bypass circuit in place of the conventional 40 µm filter. The inlet and outlet ports of the filtration device are of appropriate dimensions to engage standard connectors used in a cardiopulmonary bypass circuit. Before operation, the completed circuit is primed with fluid to exclude gas from the system. Gas initially present in the filtration device is displaced by the priming fluid and may escape from the device via the vent. Once priming is complete, the circuit is connected to the patient and blood begins to circulate through it. Blood may enter the filtration device and pass through the filter medium before re-introduction into the patient. Embodiments of this invention suitable for use in a cardiopulmonary bypass circuit are capable of handling a blood flow of up to 8 liters per minute. The filter medium is capable of removing clots, aggregates and air emboli as effectively as conventional filters, but may have the additional capability of removing specific molecular species.

The filtration device of the invention may also be incorporated into smaller scale circuits similar to those used for haemodialysis. In this setting, the filtration device may be considerably smaller than that employed in cardiopulmonary bypass, and will preferably have inlet and outlet ports suitable for connection with a haemodialysis circuit or a blood pump, through which blood can be re-circulated through a vein or artery via either two needles or one double lumen needle. This embodiment of the filtration device may be employed to treat patients suffering from various conditions, such as sepsis, in whom the removal of pro-inflammatory cytokines has been shown to be of considerable benefit. Removal of circulatory pro-inflammatory cytokines in this way may also benefit patients suffering from conditions such as inflammatory bowel disease and rheumatoid arthritis. The filtration device of this invention may also be used to remove other substances from the circulation of a patient, such as low-density lipoprotein (LDL) from patients suffering from familial hyperlipidaemia.

The flow rates encountered in these applications is considerably higher than that required for applications such as the processing of blood samples. For example, cardiopulmonary bypass in adults typically requires a flow rate of 4.5 to 6 liters per minute. At these flow rates, beads that are not securely fastened to the support medium become detached and migrate to the downstream side of the filter medium, where they may block the pores of the porous screen, potentially causing a substantial pressure drop across the filter medium, which may result in haemolysis and activation of white blood cells.

As described above, in order to overcome this problem the porous beads are preferably securely attached to the non-woven fabric. Attachment may be carried out by any suitable means, but is preferably carried out with the use of adhesives.

Thus, according to a further aspect of the invention, there is provided a method of producing a filter medium comprising a non-woven fabric having porous beads anchored to the non-woven fabric by means of adhesive, which method comprises the steps of applying adhesive to the non-woven fabric and allowing that adhesive to partially cure prior to application of the porous beads to the non-woven fabric.

This method is particularly advantageous because the partial curing of the adhesive prior to application of the porous beads avoids the adhesive being absorbed into the beads, which would block their pores and inactivate them.

The adhesive may be applied to the non-woven fabric by any method that allows the adhesive to be dispersed throughout the non-woven material, but is preferably carried out by spraying the adhesive onto the non-woven fabric. The adhesive is then allowed to partially cure before the beads are applied by a low pressure spray, or any other method that allows the beads to be dispersed throughout the non-woven fabric.

If the adhesive is allowed to cure for too long before the beads are applied, the beads will be less securely attached to the adhesive and may be more easily detached. The optimum curing time for the adhesive varies depending on the curing conditions and the type of adhesive. Typically, however, the adhesive is permitted to cure for between 5 s and 60 s, more typically between 10 s and 30 s, eg about 20 s, prior to application of the beads.

According to another aspect of the invention there is provided a method of extracorporeal blood filtration involving connecting a patient's cardiovascular circulation to an extracorporeal circulatory circuit including a filtration device according to the second aspect of the invention.

The use of the device according to the invention is advantageous in that it effectively filters the blood passing through it, removing from the blood emboli such as gas bubbles, cellular aggregates, tissue fragments, and the like. The filter medium may also be effective in removing from the blood pro-inflammatory cytokines and other pro-inflammatory molecules that are activated or generated during the surgical procedure, or that are over-produced by the body in immune system related disorders.

The method of extracorporeal blood filtration according to the invention may be used as an adjunct to a surgical procedure such as a CPB procedure. Alternatively, the method may be employed for the direct treatment of an inflammatory disease in which pro-inflammatory cytokines present in the bloodstream are implicated.

BRIEF DESCRIPTION OF THE DRAWINGS

A currently preferred embodiment of the invention will now be described, by way of illustration only, with reference to the accompanying drawings, in which:

FIG. 1 is front elevation of a blood filtration device according to this invention;

FIG. 2 is a side view of the device of FIG. 1;

FIG. 3 is an underside plan view of the device of FIG. 1;

FIG. 4 is a rear view of the device of FIG. 1;

Referring first to FIGS. 1 to 5, a filtration device according to this invention is generally designated 1. The filtration device 1 is for extracorporeal blood filtration, for instance as part of a cardiopulmonary bypass circuit.

Figure 5:
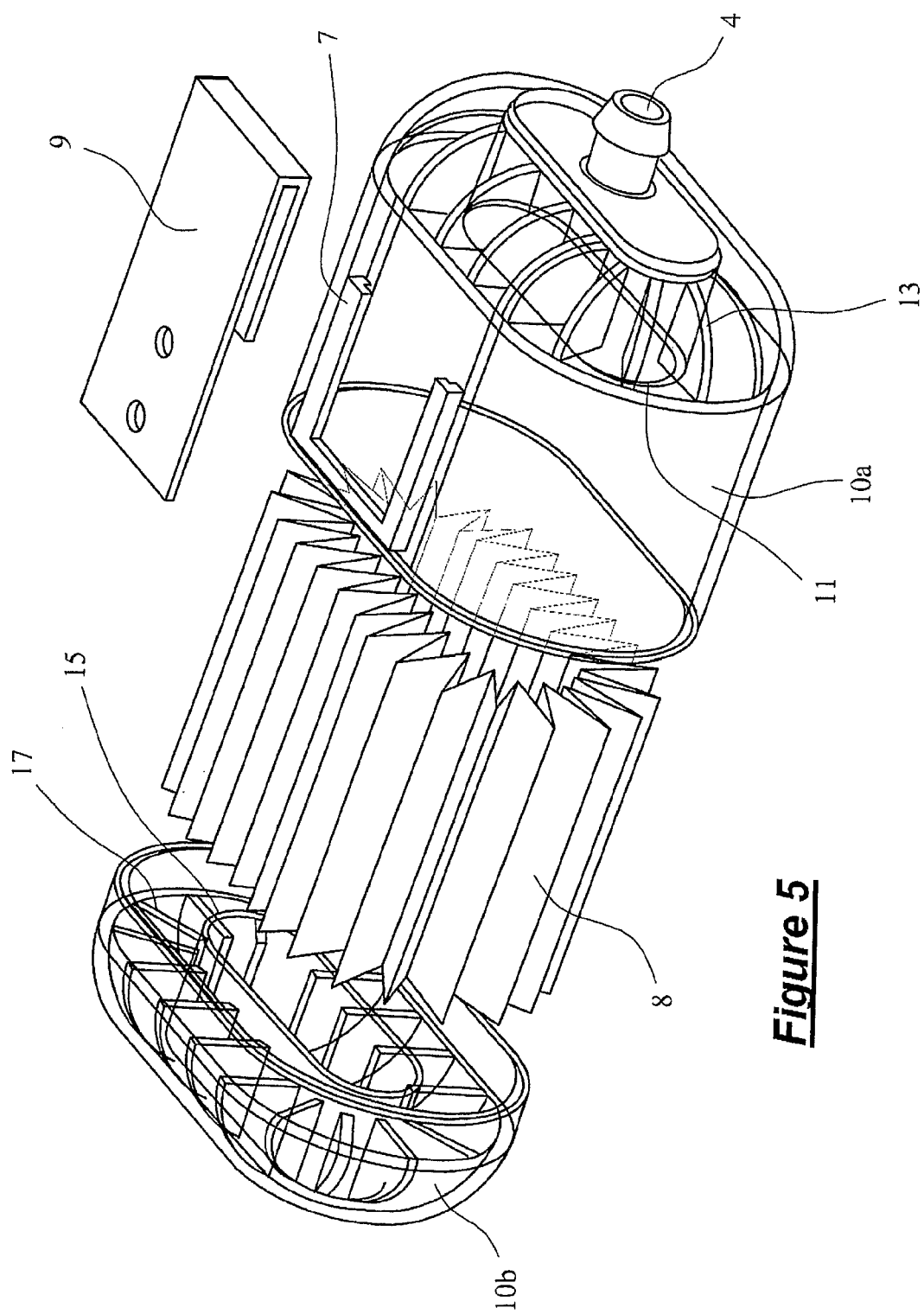
FIG. 5 is an exploded perspective view of the device of FIGS. 1 to 4.

The filtration device 1 comprises a substantially transparent housing 10 formed in plastics material. As can be seen in FIG. 5, the housing 10 consists of cooperating major and minor housing elements 10a,10b that are bonded together. An inlet port 2 is arranged tangentially to the wall of the minor housing element 10b, and an outlet port 4 is disposed in the centre of the underside of the housing 10. The top of the housing 10 is provided with a vent 6, which allows gas contained within the housing 10 to escape.

The rear of the housing 10 is provided with slot formations 7 that can be engaged with a support bracket 9 that in turn may be suspended from a suitable support.

A pleated filter medium 8 is held within the housing 10. The filter medium 8 is formed from a sheet of filter material, the construction of which is described in greater detail below, with reference to FIG. 6.

The pleated filter medium 8 is formed into a looped configuration such that it fits closely within the housing 10 and has a central lumen. An internal upstand 11 within the lower part of the major housing component 10a locates within the central lumen of the medium 8, thereby holding the medium such that the pleats of filter material are disposed around the internal periphery of the housing 10. The lower edge of the medium is supported by fins 13 that extend between the lower part of the wall of the housing 10 and the upstand 11.

The minor housing element 10b is similarly formed with a downwardly depending formation 15. The upper edge of the medium 8 abuts fins 17 that extend between the internal wall of that part of the housing 10 and the downwardly depending formation 15. The medium 8 is thus held in a substantially immobile configuration within the housing 10.

Fluid entering the housing via the inlet 2 occupies the spaces between the pleats of the medium 8 and the internal walls of the housing 10. The fluid passes through the filter medium 8 into the central lumen of the medium 8, from where it flows, via the outlet port 4, out of the device 1.

In use during a cardiopulmonary bypass procedure, the device 1 is incorporated into a blood circuit connected to an artificial heart-lung machine. The inlet port 2 and outlet port 4 are dimensioned to engage with standard connectors used in such arrangements. Prior to use, the device is primed with saline solution that is flushed through the system and thus enters the device through the inlet port 2. Air initially present in the housing 10 is displaced from the device 1 via the vent 6, such that the housing 10 becomes entirely filled with liquid. The system is then connected to the patient and blood begins to circulate through the device 1. Blood enters the housing 10 via the inlet port 2, passes through the filter medium 8 into the lumen of the medium 8, and exits the device 1 via the outlet port 4.

The effect of the filter medium 8 is to remove emboli from the blood passing through the device 1. The filter medium 8 may also be effective in removing from the blood specific molecular species, notably pro-inflammatory cytokines and other pro-inflammatory molecules that are activated or generated during the surgical procedure.

Figure 6A:
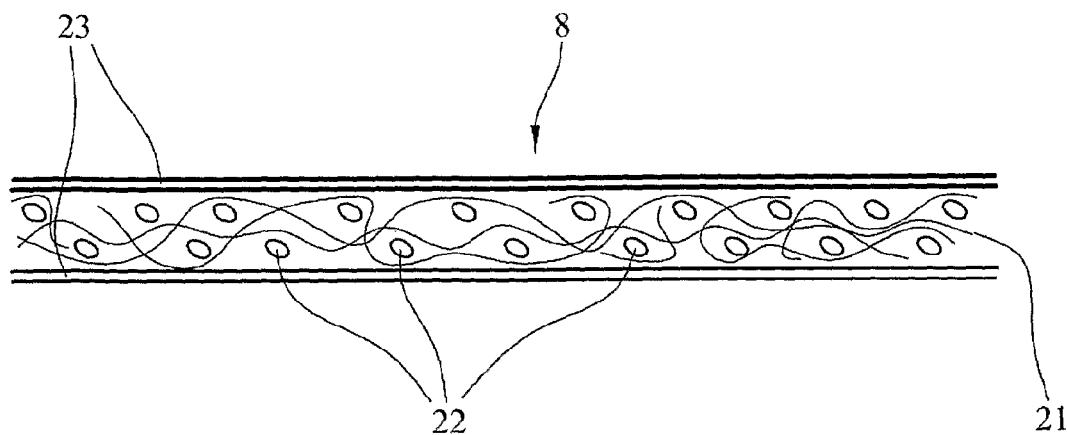
FIG. 6A is a schematic cross-sectional view of a sheet of filter material employed in the device of FIGS. 1 to 5.
Figure 6B:
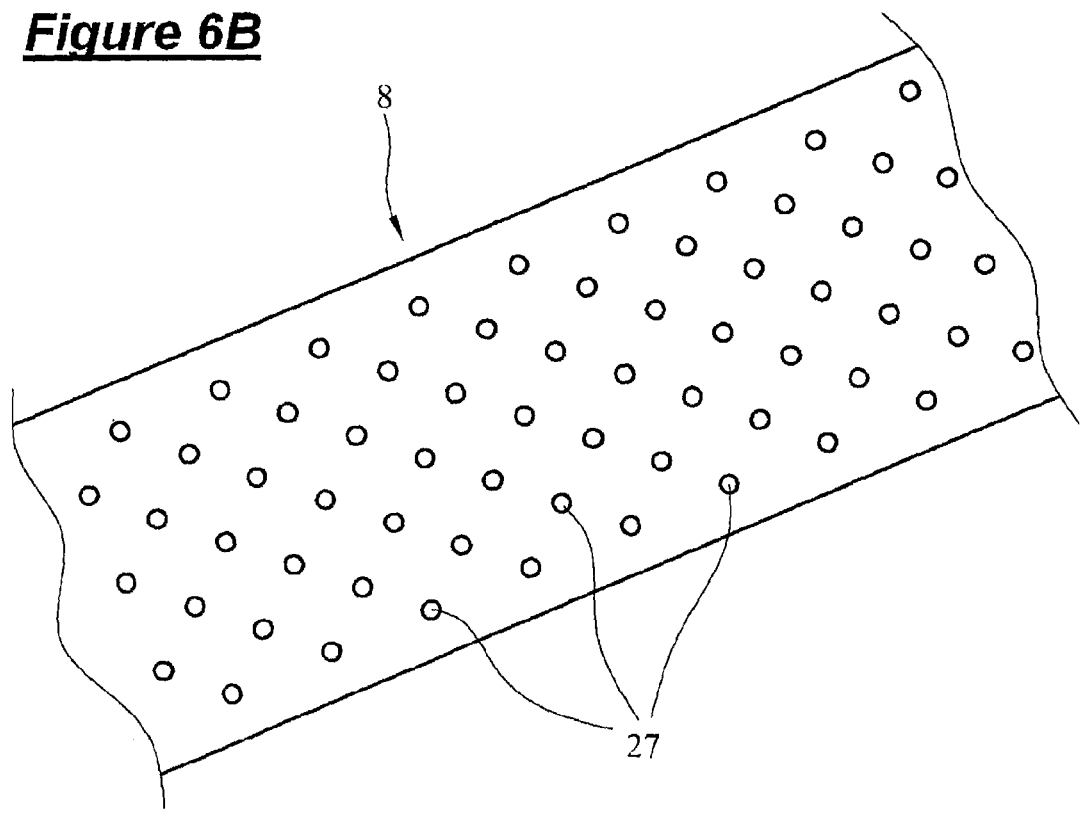
FIG. 6B is a plan view of the sheet of filter material depicted in FIG. 6A.

Referring now to FIG. 6A, a cross-sectional view of the filter medium 8 is depicted, from which it can be seen that the filter medium 8 comprises a central layer of non-woven fabric 21 impregnated with porous beads 22, sandwiched between two porous screens 23.

The filter medium 8 is produced by spraying a layer of non-woven fabric 21 with acrylic adhesive. The adhesive is then left for about 20 seconds to allow it to partially cure before the porous beads 22 are applied by a low pressure spraying device, such that the beads are dispersed throughout the non-woven fabric 21. The adhesive is then allowed to cure completely.

Porous screens 23 of polyester sheet are then applied to both sides of the bead-impregnated fabric 21, and the three layers are bonded together by ultrasonic welding in such a way as to completely encapsulate the fabric 21 between the screens 23, forming a sheet of the filter medium 8. Ultrasonic welding is carried out such that the layers of the filter medium 8 are welded together only at points 27 that are arranged in a regular array throughout the full extent of the sheet (see FIG. 6B). The filter medium 8 is cut to size and pleated, and the ends of the pleated sheet are joined to form a loop of the filter medium 8, which may then be inserted into a filtration device 1.

Figure 7:
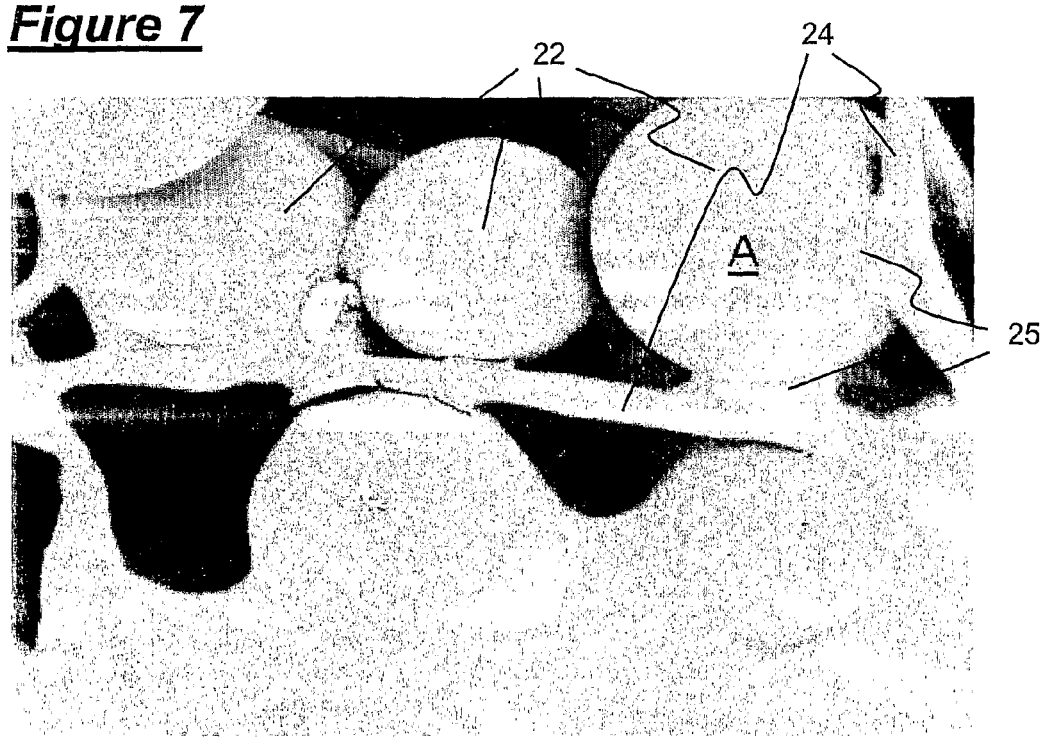
FIG. 7 is an electron micrograph showing porous beads attached to the fibres of a non-woven fabric by an adhesive.
Figure 8:
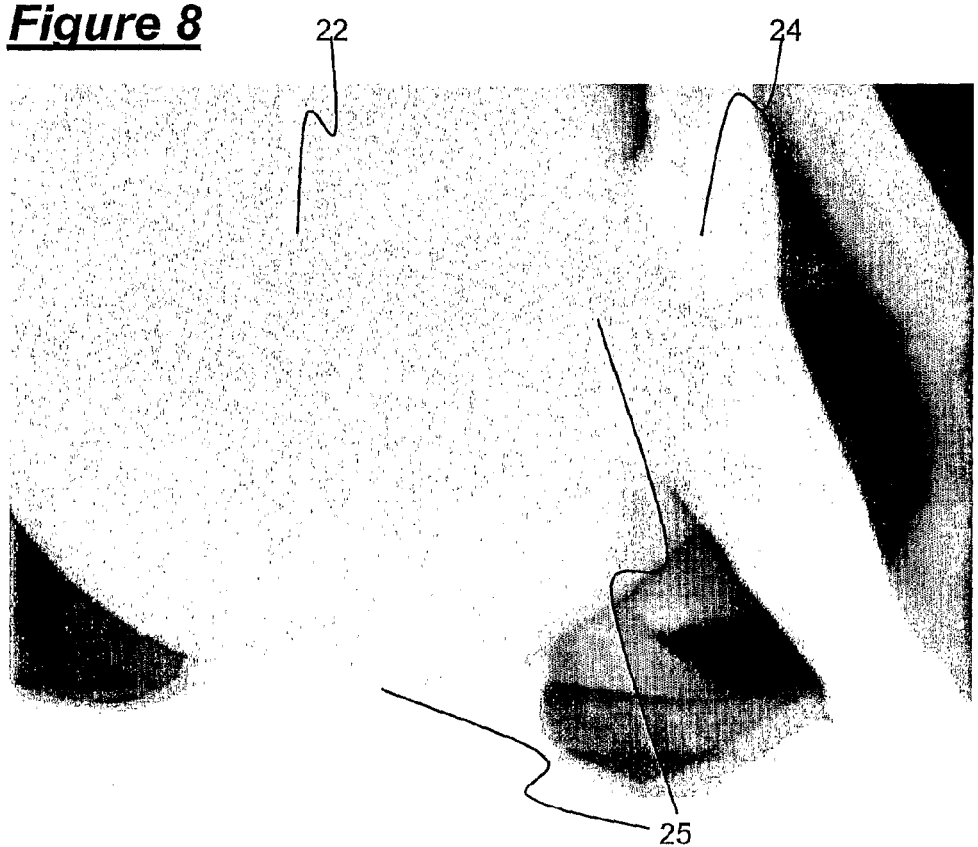
FIG. 8 is a view on enlarged scale of the region marked A in FIG. 7.

Referring now to FIGS. 7 and 8, an electron micrograph of bead impregnated non-woven fabric is shown. The beads 22 attach to individual fibres 24 of the non-woven fabric 21 via adhesive pedicles 25. The irregular fibre structure of the non-woven fabric 21 allows each bead 22 to attach to a number of fibres 24, providing stronger attachment and reducing the likelihood of their detachment under high flow rate conditions. This is illustrated most clearly in FIG. 8, where a porous bead 22 is attached to multiple fibres 24 via adhesive pedicles 25.

Tissue water content is an indication of the magnitude of an inflammatory response. Tissue water content is quantified by calculating the dry weight of a tissue sample as a proportion of its wet weight, with lower values indicating higher tissue water content, and a greater inflammatory reaction, and higher values indicating a lower tissue water content and therefore lower inflammation.

Figure 9:
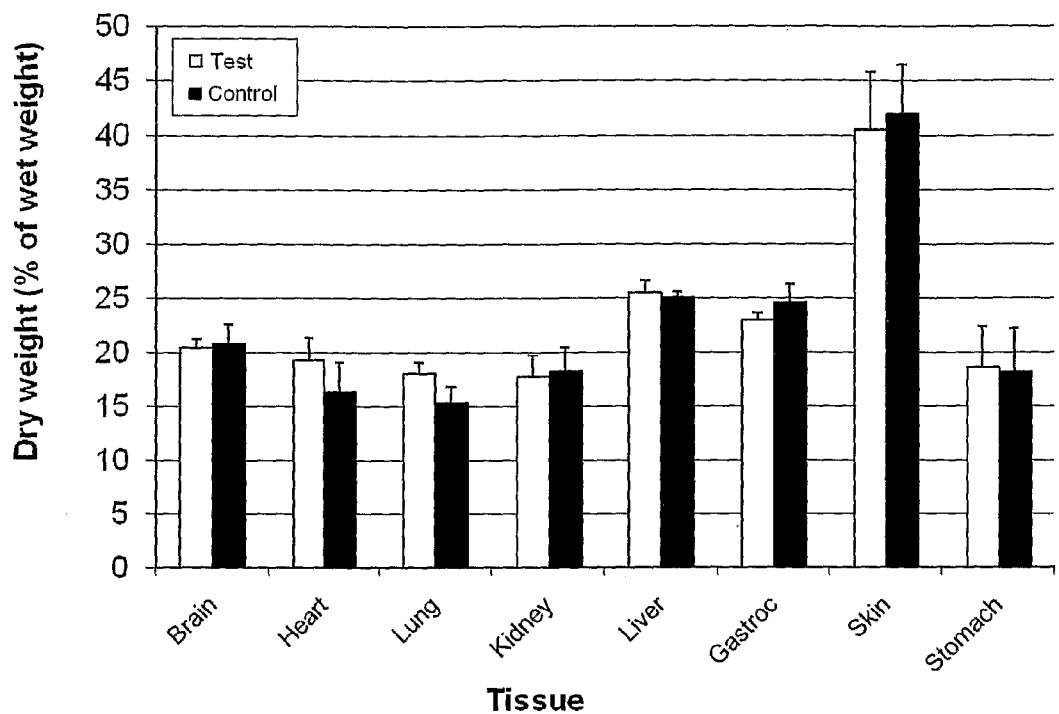
FIG. 9 shows the dry weight of a number of tissue types following cardiopulmonary bypass, either without filtration (control), or with a blood filtration device according to this invention (test)

FIG. 9 is a comparison of the tissue water content of control and test groups, with the control group having undergone CPB without a filter device, and the test group having undergone CPB with a blood filtration device of this invention. There is a statistically significant difference between the two groups in relation to lung tissue. This is of particular significance given that fluid build up in the lungs is a pathology particularly associated with excessive inflammation. The reduced water content of lung tissue brought about by the blood filtration device of this invention therefore indicates a significant advantage over standard methods of performing CPB in reducing inflammation-related pathologies.

The applicant believes that the blood filtration device of this invention is able to reduce the water content of lung tissue following CPB by removing pro-inflammatory cytokines from the circulation.

Figure 10A:
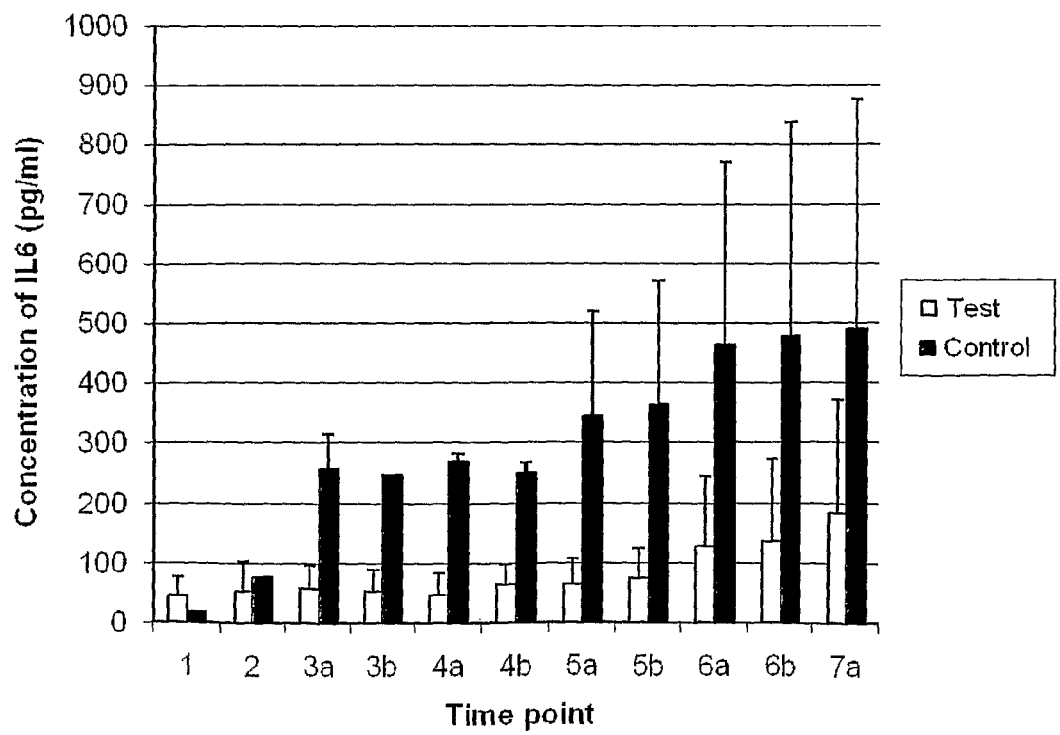
FIGS. 10A-10C show circulatory cytokine levels in subjects at a number of time points during and after cardiopulmonary bypass, either without filtration (control), or with a blood filtration device according to this invention (test).
Figure 10B:
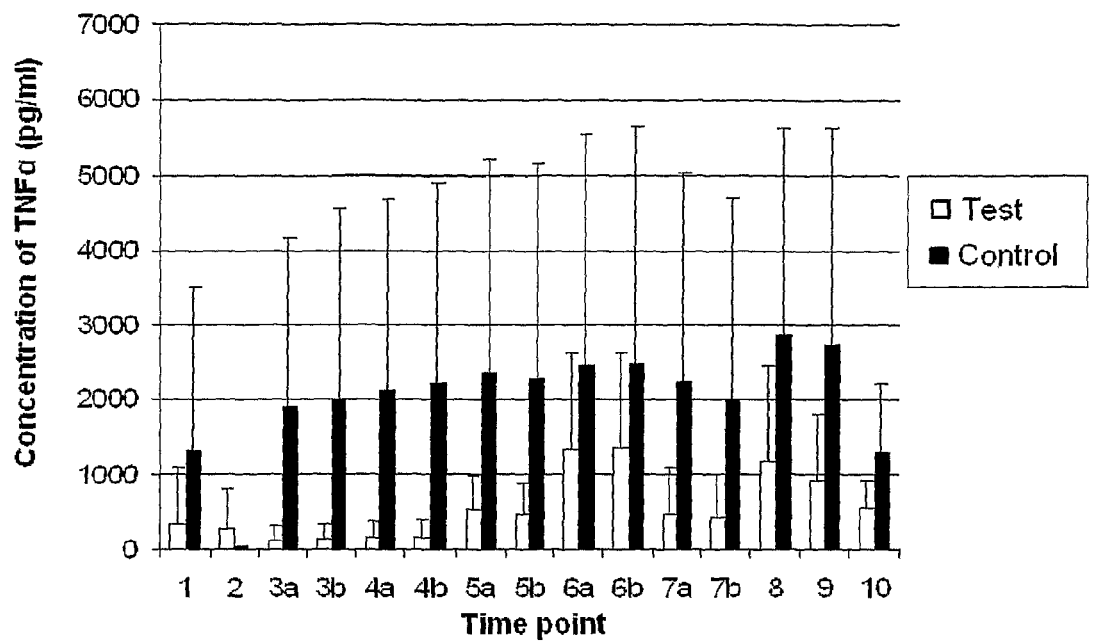
Figure 10C:
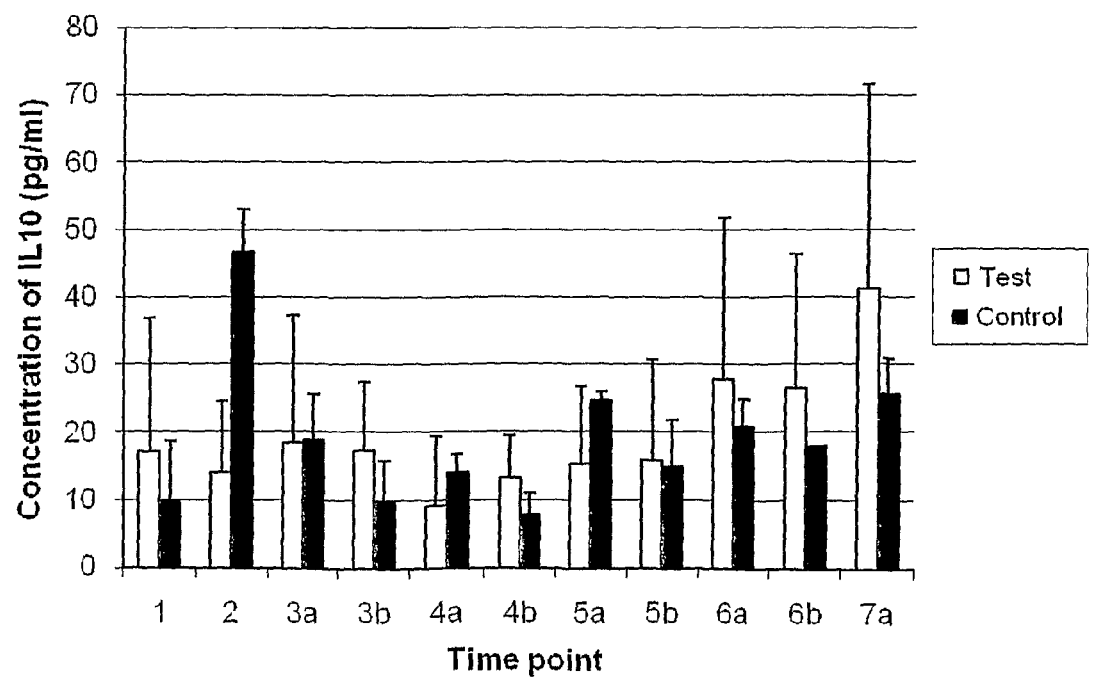

FIGS. 10A-10C show cytokine levels in control and test groups at various time points during and following CPB, with the control group having undergone CPB without a filter device, and the test group having undergone CPB with a blood filtration device of this invention, as above. The specific cytokines measures were the pro-inflammatory cytokines Interleukin-6 (IL-6) and Tumour Necrosis Factor alpha (TNF•), shown in FIGS. 10A and 10B respectively, and anti-inflammatory cytokine Interleukin-10 (IL-10), shown in FIG. 10C.

There is a clear and statically significant reduction in the levels of pro-inflammatory cytokines IL-6 and TNF• in the test group as compared to the control group (FIGS. 10A and 10B). In contrast, there is no statistically significant difference in the level of anti-inflammatory cytokine IL-10 (FIG. 10C) between the test and control groups.

The results indicate that the blood filtration device of this invention has the capacity to reduce the inflammation resulting from CPB by selectively removing pro-inflammatory cytokines from the circulation.

The invention claimed is:

1. A cardiopulmonary bypass circuit including a filtration device comprising a housing having inlet and outlet ports connected in fluid communication with the cardiopulmonary bypass circuit and a filter medium disposed in a blood flow path of the cardiopulmonary bypass circuit between said inlet and outlet ports, wherein the filter medium comprises a single layer of non-woven fabric having a weight of up to 500 g/m$^2$ and porous beads anchored to fibres of the non-woven fabric by means of adhesive and the filtration device further comprises a porous screen having pores of between 20 μm and 100 μm in diameter on at least a downstream side of the filter medium, wherein the porous beads have a greater diameter than the pores of the porous screen.

2. A cardiopulmonary bypass circuit according to claim 1, wherein the non-woven fabric is a thermally bonded airlaid non-woven fabric.

3. A cardiopulmonary bypass circuit according to claim 1, wherein the non-woven fabric is formed of polyester fibres.

4. A cardiopulmonary bypass circuit according to claim 1, wherein the non-woven fabric has a weight of between 20 g/m$^2$ and 200 g/m$^2$.

5. A cardiopulmonary bypass circuit according to claim 1, wherein the adhesive is acrylic adhesive.

6. A cardiopulmonary bypass circuit according to claim 1, wherein the porous screen is formed of woven polyester.

7. A cardiopulmonary bypass circuit according to claim 1, wherein a second porous screen is provided on an upstream side of the filter medium.

8. A cardiopulmonary bypass circuit according to claim 1, wherein the porous beads are formed out of porous carbon, pyrolysed polymer, or zeolite.

9. A cardiopulmonary bypass circuit according to claim 8, wherein the porous beads are mesoporous carbon beads formed of polymeric carbon.

10. A cardiopulmonary bypass circuit according to claim 1, wherein the diameter of the porous beads is between 50 μm and 500 μm.

11. A cardiopulmonary bypass circuit according to claim 1, wherein the porous beads are loaded into the non-woven fabric at a density of between 0.2 and 10 g/m$^2$.

12. A cardiopulmonary bypass circuit according to claim 1, wherein the filter medium has a pleated configuration.

13. A cardiopulmonary bypass circuit according to claim 1, wherein the overall surface area of the filter medium is in excess of 0.01 m$^2$.

14. A cardiopulmonary bypass circuit according to claim 1, wherein the filter medium is formed into an annular configuration with a central lumen.

15. A cardiopulmonary bypass circuit according to claim 1, wherein the housing comprises a vent.

16. A cardiopulmonary bypass circuit according to claim 1, wherein the porous beads comprise a porous nanostructure.

17. A cardiopulmonary bypass circuit according to claim 1, wherein the cardiopulmonary bypass circuit accommodates a blood flow rate of up to 8 liters per minute.

18. A cardiopulmonary bypass circuit according to claim 1, wherein the cardiopulmonary bypass circuit accommodates a blood flow rate of 4.5 to 6 liters per minute.

\* \* \* \* \*